United States Patent

Auman et al.

[11] Patent Number: 5,286,841
[45] Date of Patent: Feb. 15, 1994

[54] FLUORINE-CONTAINING DIAMINES, POLYAMIDES, AND POLYIMIDES

[75] Inventors: Brian C. Auman, Newark; Andrew E. Feiring, Wilmington, both of Del.

[73] Assignee: E. I. Du Pont de Nemours and Company, Wilmington, Del.

[21] Appl. No.: 944,587

[22] Filed: Sep. 14, 1992

Related U.S. Application Data

[62] Division of Ser. No. 750,800, Aug. 27, 1991, Pat. No. 5,175,307.

[51] Int. Cl.$^5$ .................. C08G 69/26; C08G 73/10
[52] U.S. Cl. ................... 528/353; 528/125; 528/128; 528/170; 528/172; 528/173; 528/174; 528/176; 528/183; 528/185; 528/188; 528/220; 528/229; 528/350
[58] Field of Search ............. 528/353, 125, 128, 170, 528/172, 173, 174, 176, 185, 188, 183, 220, 229, 350

[56] References Cited

U.S. PATENT DOCUMENTS

| | | | |
|---|---|---|---|
| 4,530,993 | 7/1985 | Jinda et al. | 528/353 |
| 5,087,691 | 2/1992 | Harris | 528/353 |
| 5,089,593 | 2/1992 | Fjare et al. | 528/353 |
| 5,177,176 | 1/1993 | Auman | 528/353 |
| 5,194,579 | 3/1993 | Numata et al. | 528/353 |
| 5,202,410 | 4/1993 | Irwin | 528/353 |

FOREIGN PATENT DOCUMENTS

| | | |
|---|---|---|
| 62-176135 | 1/1987 | Japan . |
| 62-280257 | 5/1987 | Japan . |
| 91/01340 | 2/1991 | World Int. Prop. O. . |

OTHER PUBLICATIONS

Cassidy, P. E., et al., Macromol. Sci., Rev. Macromol. Chem. Phys., C29, 365 (1989).
Rogers, H. G., et al., Macromolecules, 18, 1058–1068 (1985).
Harris, F. W., et al., Polym. Preprints, 31(1), 342 (1990).

*Primary Examiner*—John Kight, III
*Assistant Examiner*—P. Hampton-Hightower

[57] ABSTRACT

This invention concerns novel fluorine-containing diamines, polyamides and polyimides. The compounds are useful in the formation of moisture resistant films, fibers and shaped articles.

6 Claims, No Drawings

FLUORINE-CONTAINING DIAMINES, POLYAMIDES, AND POLYIMIDES

This is a division of Ser. No. 07/750,800, filed on Aug. 27, 1991, now U.S. Pat. No. 5,175,367.

BACKGROUND OF THE INVENTION

1. Field of the Invention

The present invention concerns novel fluorine-containing diamines as well as polyamides and polyimides prepared from the diamines. The compounds disclosed are useful in the formation of moisture resistant films, fibers and other shaped articles.

2. Technical Background

Fluorine-containing diamines, polyimides and polyamides are well-known in the art; examples can be found in a review article (Cassidy, P. E.; Aminabhavi, T. M.; Farley, J. M. J., Macromol. Sci., Rev. Macromol. Chem. Phys., C29, 365 (1989)) and other recent references.

Rogers, H. G.; Gaudiana, R. A.; Hollinsed, W. C.; Kalyanaraman, P. S.; Manello, J. S.; McGowan, C.; Minns, R. A.; Sahatjian, R., Macromolecules, 18, 1058–1068 (1985), disclose 2,2'-trifluoromethylbenzidine and polyamides.

Harris, F. W.; Hsu, S. L.-C.; Tso, C. C., Polym. Preprints, 31 (1), 342 (1990) disclose polyimides.

WO 91/01340, published on Feb. 7, 1991, discloses diamines of the below formula:

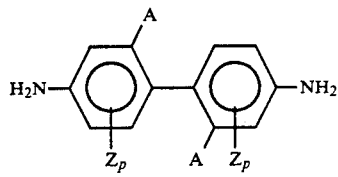

wherein each A is a substituent other than H, each Z is a H or substituent other than H and each P is an integer having a value 1 to 3, said A and Z being present in sufficient amount to provide said diamine with a noncoplanar molecular structure.

Japanese Kokai Patent Application No. SHO 62 [1987]-280257 discloses a low-viscosity varnish, which can form a low-thermal expansion resin material when treated by heating.

Japanese Kokai Patent SHO 62 [1987]-176135 concerns an etching method for etching resin film having a low thermal expansion coefficient, using polyimide resin materials.

SUMMARY OF THE INVENTION

This invention provides a novel fluorinated aromatic diamine of the structure I,

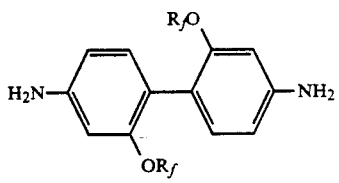

wherein $R_f$ is a linear or branched perfluorinated alkyl group containing 1–18 carbon atoms or where said perfluorinated alkyl group has one F atom replaced by hydrogen and/or one F atom replaced by chlorine, $R_f$ optionally containing at least one or more ether oxygens between alkyl segments. Preferably $R_f$ is perfluorinated; most preferably $R_f$ is $CF_3$.

Also provided are novel polyamides and polyimides prepared from these diamines. The polyamides comprise the repeat unit:

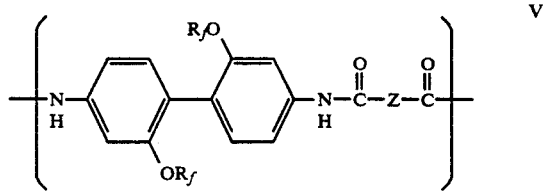

wherein $R_f$ is as defined above, and Z is a hydrocarbylene or a substituted hydrocarbylene. The polyimides comprise the repeat unit

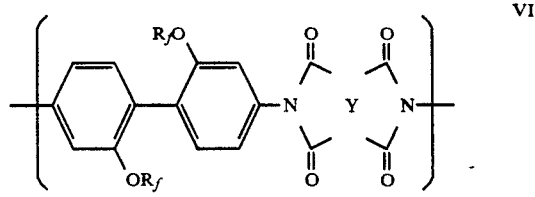

wherein $R_f$ is as defined above and Y is a tetravalent hydrocarbyl group or a substituted tetravalent hydrocarbyl group.

DETAILED DESCRIPTION OF THE INVENTION

The fluorinated diamines of the present invention may be prepared by known processes, for example, by reduction of 3-nitro-1-($OR_f$)benzenes (II) with sodium borohydride in dimethylsulfoxide to the hydrazine derivatives (III), followed by benzidine rearrangement using an acid catalyst, such as concentrated hydrochloric acid.

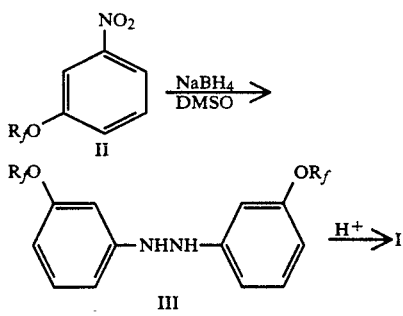

The conversion of nitroaromatics to the corresponding hydrazine derivatives (via azoxy or azo intermediates) and subsequently to diamines (benzidine rearrangement) is well known in the art, and numerous procedures have been described in, for example, Vogel, A. I., *A Textbook of Practical Organic Chemistry*, 3rd Ed, Longman Group Ltd., London, pp. 628–634, 1956.

The art discloses several procedures for preparing 3-nitro-1-($OR_f$)benzenes (II) from 3-nitrophenol. For example, 3-nitro-1-(trifluoromethoxy)benzene may be prepared by reaction of 3-nitrophenol with carbon tetrachloride and hydrogen fluoride as described in Feiring, A. E., U.S. Pat. No. 4,157,344 (1979); J. Org. Chem., 44, 1252, 1979. More generally, 3-nitro-1-(OR$_f$)-benzenes may also be prepared as described by Sheppard, W. A., J. Org. Chem., 29, 1, 1964, by reaction of esters of 3-nitrophenol with sulfur tetrafluoride. Phenolic compounds are also known to react with fluorine-containing olefins, such as tetrafluoroethylene or perfluoroalkylvinyl ethers, in the presence of base to give fluorine-containing ethers; references include England, D. C., et al., J. Amer. Chem. Soc., 82, 5116, 1960, and Massardo, P. et al., Eur. Pat. Appl. EP 271 923 (1987). In a variation of this procedure, disclosed herein, the 3-nitro-(chloroperfluoroalkoxy)benzene (Compound IV) is prepared by reaction of 3-nitrophenolate with perfluoropropyl perfluorovinyl ether and hexachloroethane.

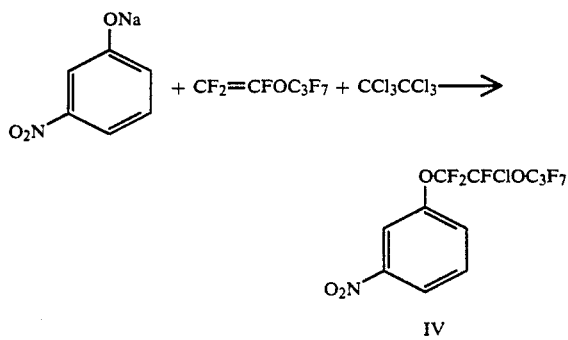

Polyamide and polyimide homopolymers may be prepared from the diamines (I) of this invention by known condensation polymerization reactions. Thus, polyamides (V) can be prepared by the known reaction of a diamine with a dicarboxylic acid of structure HO$_2$C—Z—CO$_2$H, where Z is as defined above, or with any polymerizable derivative thereof, e.g., diacid chloride, such as terephthaloyl chloride, in the presence of dipolar aprotic solvents such as, but not limited to, N,N-dimethyl formamide, N,N-dimethyl acetamide, and N-methyl pyrrolidone. General procedures for preparing polyamides are well known in the art and can be found in references such as Yang, H. H., *Aromatic High-Strength Fibers*, Wiley-Interscience, New York, pp. 111–115 and 128–137, 1989. The group Z in Structure V can be any hydrocarbylene moiety. Examples of Z are m- and p-phenylene, hexamethylene, naphthalene (e.g., 2,6-naphthalene), 2,2-bis(4-carboxyphenyl)hexafluoropropane and 4,4'-biphenylene.

Polyimides (VI) are prepared by the known reaction of a diamine with a dianhydride of structure

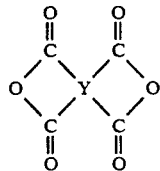

wherein Y is a tetravalent hydrocarbyl group, or from any precursors thereof, such as tetracarboxylic acids or their derivatives, in the presence of a dipolar aprotic solvent, such as one mentioned below, to form a poly(amic acid), followed by thermal or chemical imidization. The polymerization can also be done without isolation of the poly(amic acid).

Examples of suitable dianhydrides include, but are not limited to, 2,2-bis(3,4-dicarboxyphenyl)hexafluoropropane dianhydride, pyromellitic anhydride, 1,4,5,8-naphthalenetetracarboxylic dianhydride, 2,3,6,7-naphthalenetetracarboxylic dianhydride, 3,3',4,4'-biphenyltetracarboxylic dianydride, 1,2,5,6-naphthalenetetracarboxylic dianhydride, 2,2'3,3'-biphenyltetracarboxylic dianhydride, 3,3',4,4'-benzophenonetetracarboxylic dianhydride, 2,2-bis(3,4-dicarboxyphenyl)propane dianhydride, bis(3,4-dicarboxyphenyl)sulfone dianhydride, 3,4,9,10-perylenetetracarboxylic dianhydride, 1,1-bis(2,3-dicarboxyphenyl)ethane dianhydride, 1,1-bis(3,4-dicarboxyphenyl)ethane dianhydride, bis(2,3-dicarboxyphenyl)methane dianhydride, bis(3,4-dicarboxyphenyl)methane dianhydride, oxydiphthalic dianhydride, 9-trifluoromethyl-9-phenyl-2,3,6,7-xanthenetetra-carboxylic dianhydride, 9,9-bis(trifluoromethyl)xanthenetetracarboxylic dianhydride, 12,14-(R)2-12,14-(R$_f$)2-12H,14H-5,7-dioxa-2,3,9,10-pentacenetetracarboxylic acid dianhydride (wherein R is selected from the group consisting of aryl, substituted aryl, and perfluoroalkyl, and R$_f$ is perfluoroalkyl).

Suitable solvents for carrying out the polymerization reactions include, but are not limited to, polar organic solvents, such as sulfoxide type solvents, including dimethylsulfoxide and diethylsulfoxide; formamide type solvents, such as N,N-dimethylformamide, N,N-diethylformamide; acetamide type solvents, including N,N-dimethylacetamide, N,N-diethylacetamide; pyrrolidone type solvents, including N-methyl-2-pyrrolidone, N-cyclohexyl-2-pyrrolidone, 1,3-dimethyl-2-imidazolidinone, N-vinyl-2-pyrrolidone; phenolic solvents including phenol, o-, m-, p-cresol, xylenol, halogenated phenol, catechol; hexamethylphosphoramide; and a number of lactones including γ-butyrolactones. These solvents may be used alone or as a mixture. Partial use of aromatic hydrocarbons, such as xylene and toluene, is also possible, and sometimes desirable, when, for example, removal of water as an azeotrope is desired.

General procedures for preparing polyimides are well known and can be found in references such as Yang, H. H., *Aromatic High-Strength Fibers*, Wiley-Interscience, New York, pp. 676–685, 1989.

Polyamide or polyimide copolymers may also be made using the diamines of the present invention. For example, polyimide copolymers may be made using a diamine selected from the diamines of this invention and another diamine, including, for example, another diamine of this invention or bis(4-aminophenyl)ether, 4,4'-diamino-3,3'-dimethylbiphenyl, 4,4'-diamino-3,3'-dimethoxybiphenyl, 4,4'-bis(4-aminophenoxy)biphenyl, diaminodiphenylsulfone, bis[4-(4-aminophenoxy)phenyl]sulfone, bis[4-(3-aminophenoxy)phenyl]sulfone, bis[4-(2-aminophenoxy)phenyl]sulfone, 1,4-bis(4-aminophenoxy)benzene, 4,4'-diamino-2,2'-dichloro-5,5'-dimethoxybiphenyl, 4,4'-diamino-2,2',5,5'-tetrachlorobiphenyl, 9,10-bis(4-aminophenyl)anthracene, o-tolidine sulfone, 1,3-bis(4-aminophenoxy)benzene, 1,3-bis(3-aminophenoxy)benzene, 1,4-bis(4-aminophenyl)benzene, [4-(4-aminophenoxy)phenyl]ether, bis(4-aminophenyl)methane, bis(4-amino-3-ethylphenyl)methane, bis(4-amino-3-methylphenyl)methane, bis(4-amino-3-chlorophenyl)methane, bis(4-aminophenyl)sulfide, bis(3-aminophenyl)ether, 3,4'-diaminodiphenyl ether, 4,4'-bis[4-(4-aminophenoxy)phenyl]propane, 2,2-bis[4-(4- aminophenoxy)phenyl]hexafluoropropane, 2,2-bis(4-aminophenyl)propane, 2,2-bis(4-aminophenyl)hexafluoropropane, 2,2-bis(4-amino-3-hydroxyphenyl)propane, 2,2-bis(4-amino-3-hydroxyphenyl)hexafluoropropane, 9,9-bis(4-aminophenyl)-10-hydroanthracene, diaminoanthraquinones (e.g., 1,5-diamino-9,10-anthraquinone and 2,6-diaminoanthraquinone), 4,4'-diamino-3,3'-dichlorobiphenyl, 4,4'-diamino-3,3'-dihydroxybiphenyl, 4,4'-diaminobiphenyl, 9,9-bis(4-aminophenyl)fluorene, bis(3-amino-4-methylphenyl)sulfone, 2-(4-aminobiphenyl)-2-[3-(4-aminophenoxy)phenyl]propane, Bisaniline M, Bisaniline P, bis(4-amino-2,6-methylphenyl)methane, 2,4-diamino-1-isopropylbenzene, 1,4-diamino-2,5-dichlorobenzene, 1,4-diamino-2,6-dichlorobenzene, 1,4-diamino-2,5-dimethylbenzene, 1,4-diamino-2-chlorobenzene, 1,3-diamino-4-chlorobenzene, 1,4-diamino-5-chloro-2-methylbenzene, 6-aceto-2,4-diamino-1,3,5-triazine, 1,4-diamino-2,3,5,6-tetramethylbenzene, 1,3-diamino-2,4,6-trimethylbenzene, bis(3-aminopropyl)tetramethyldisiloxane, 2,7-diaminofluorene, 2,5-diaminopyridine, 1,4-diaminobenzene, 1,2-bis(4-aminophenyl)ethane, 4,4'-diaminobenzanilide, 4-aminophenyl 4-aminobenzoate, 1,5-diaminonaphthalene, 2,4-diaminotoluene, 1,3-diamino-5-trifluoromethylbenzene, 1,3-bis(4-aminophenyl)hexafluoropropane, 1,4-bis(4-aminophenyl)octafluorobutane, 1,5-bis(4-aminophenyl)decafluoropentane, 1,7-bis(4-aminophenyl)tetradecafluoroheptane, 2,2-bis[4-(3-aminophenoxy)phenyl]hexafluoropropane, 2,2-bis[4-(2-aminophenoxy)phenyl]hexafluoropropane, 2,2-bis[4-(4-aminophenoxy)-3,5-dimethylphenyl]hexafluoropropane, 2,2-bis[4-(4-aminophenoxy)-3,5-bis(trifluoromethyl)phenyl]hexafluoropropane, 1,4-bis(4-amino-2-trifluoromethylphenoxy)benzene, 4,4'-bis(4-amino-2-trifluoromethylphenoxy)biphenyl, 4,4'-bis(4-amino-3-trifluoromethylphenoxy)biphenyl, 4,4'-bis(4-amino-2-trifluoromethylphenoxy)diphenyl sulfone, 4,4'-bis(3-amino-3-trifluoromethylphenoxy)diphenyl sulfone, 2,2-bis[4-(4-amino-3-trifluoromethylphenoxy)phenyl]hexafluoropropane, 4,4'-diamino-3,3'5,5'-tetramethylbiphenyl, 4,4'-diamino-2,2'-3,3',5,5'bis(trifluoromethyl)biphenyl, 4,4'-diamino-2,2'-dimethylbiphenyl, 4,4'-diamino-3,3'-dimethylhexafluorobiphenyl, 4,4'''-diaminoquaterphenyl, 1,3-diamino-5-tert-butylbenzene, 1,4-bis(3-aminophenoxy)benzene, bis[4-(3-aminophenyl)-phenyl]ether, 4,4'-diamino-2,2'-dichlorobiphenyl, 3,3'-diamino-4,4'-dihydroxybiphenyl, and mixtures thereof. Polyimide copolymers may also be made from a mixture of two or more tetra-functional organic moieties (e.g., dianhydrides) with a single diamine or with mixed diamines.

Polyamide copolymers can be made similarly from one or a mixture of diamines, with one, or a mixture of dicarboxylic acids or polymerizable derivitives thereof.

Functional groups that are useful for crosslinking may be incorporated into the polyamide and polyimide chains using procedures such as those provided in "Addition Polyimides," I. K. Varma et al., Polymer News, 12, pp. 294–306 (1987); and "Recent Advances in Thermosetting Polyimides," H. Stenzenberger, British Polymer Journal, 20, 383–396 (1988). Generally, the desired functional group can be added as a monoamine or monoanhydride (e.g., maleic anhydride) and functions as an endcapping group, usually for lower molecular weight polymer chains. The chosen functional group can be added at the start, during, or at the end of polymerization, so as to cap the remaining reactive groups and give functional chain ends that subsequently can react with each other or with other added groups to give a crosslinked structure. The polymers are typically thermally cured to effect crosslinking. In addition, where desired, crosslinking may also be performed photochemically, with or without added catalysts or promotors (e.g., in the case of styrene, termination with or without, e.g., benzophenone, as photosensitizer), or thermally with the aid of initiators such as benzoyl peroxide and 2,2'-azobis(isobutyronitrile). Such functionalization can be used in the poly(amic acid) form, as a derivative (e.g., a poly(amic ester)), or as a polyimide, provided the polyimide is soluble or otherwise processible. It is also possible to add such a functional group along the chain in the polymer by copolymerizing the polyimide of the present invention with a difunctional diamine or dianhydride that contains such a functional crosslinking group (e.g., 1,2-bis(3-aminophenyl)acetylene).

Examples of functional groups useful for crosslinking of "addition-type" polyimides include maleimide, nadimide, phenylacetylene (ethynylphenyl), styrene, biphenylene, benzocyclobutene, paracyclophane, benzonitrile, as well as other groups capable of reacting with each other to give a crosslinked structure.

The fluorine-containing polyamides and polyimides of this invention are useful for the formation of films, fibers, and other shaped articles having high thermal stability, low thermal expansion coefficient, high optical clarity, low dielectric constant, and moisture resistance. The fluorine containing polyimides of this invention often have improved solubility which is important for polyimide processing, especially when it is desirable not to pass through a poly(amic acid) intermediate. In addition, the rigid-rod nature of the monomer intermediate is important for providing high strength/high modulus fibers as well as films having low coefficients of thermal expansion. Fluorinated diamines are useful as monomers to make the above polymers. The $OR_f$ groups in the 2,2'-positions of the fluorinated diamines of Structure I give the monomers stability in concentrated sulfuric acid, which is used in the manufacture of several commercially important polyamides, due to the presence of the fluorine on the chains. In addition, the $OR_f$ groups in the 2,2'-positions will cause the benzene-benzene rings in the diamines to twist sterically relative to one another, thus imparting special properties to the polymers prepared therefrom.

In addition to preparation of polyamides and polyimides, the diamines of this invention are also useful in other polymers, such as poly(amide-imides), and as curing agents for epoxides.

EXAMPLES

EXAMPLE 1

Synthesis of 4,4'-Diamino 2,2'-bis(trifluoromethoxy)biphenyl

A flame-dried 5-L flask, equipped with a mechanical stirrer, addition funnel, and thermometer was charged under $N_2$ with 1 L of dimethylsulfoxide (DMSO). The flask was cooled in an ice water bath and 167.2 g (4.42 mol) of sodium borohydride was slowly added so that the temperature was maintained at 18°–20° C. To this stirred mixture was added 155 g (0.75 mol) of 3-nitrotrifluoromethoxybenzene in 300 mL of DMSO over a period of 0.25 h. An additional 100 mL of DMSO was used to rinse the addition funnel. The cooling bath was removed, allowing the mixture to warm exothermally in stages to about 65° C., after which it began to cool spontaneously. The mixture was then heated to 92° C. over about 1 h and then allowed to cool to room temperature. Total reaction time was about 3.5 h. The mixture was cooled to 0° C. and 1 L of methylene chloride was added, followed by the slow addition of 1.5 L of 10% hydrochloric acid. Additional water was added to fill the flask and the mixture was stirred for 1 h. The methylene chloride layer was separated and the aqueous layer extracted with 500 mL of methylene chloride. The combined organic extracts were washed with 2×500 mL of water, 1×500 mL of 10% hydrochloric acid, and 1×500 mL of water, dried over anhydrous magnesium sulfate, filtered, and concentrated on a rotary evaporator to 123.6 g of an orange oil whose structure is assigned as N,N'-bis(3-trifluoromethoxyphenyl)-hydrazine, $^1$H NMR ($\delta$, CDCl$_3$) 5.7 (s, 2H), 6.7 (m, 4H), 7.2 (t, 2H), $^{19}$F NMR −58.14 ($\delta$, CDCl$_3$). The same compound from other preparations showed a strong infrared absorption at 3340 cm$^{-1}$.

The crude product from the above preparation was dissolved in 200 mL of ether and added over 1.25 h to a stirred mixture of 700 mL 6N hydrochloric acid, 100 g anhydrous tin(II) chloride, and 200 mL ether at 0° C. The mixture was stirred for 1 h at 0° C. and 100 mL of concentrated hydrochloric acid was added. Stirring was continued overnight at room temperature. The resulting mixture was cooled to 0° C., treated With 400 mL of concentrated hydrochloric acid, and filtered. The solid was recrystallized from aqueous HCl with Darco ® treatment and suspended in 800 mL of water at 0° C. Aqueous sodium hydroxide (20%, 300 mL) was added, followed by 800 mL of ether, and the mixture was stirred until all solids had dissolved. The ether layer was separated and the aqueous layer was extracted with additional ether. The combined ether extracts were dried over anhydrous magnesium sulfate and concentrated on a rotary evaporator to an oil. The oil was dissolved in a mixture of methylene chloride and ether and saturated with gaseous hydrogen chloride. The solid was collected and rinsed with ether. This amine hydrochloride salt was recrystallized and converted to the free diamine as described above. Kugelrohr distillation of the free amine at 140°–145° C. and 0.3 mm pressure gave 80.8 g (65%) of 4,4'-diamino-2,2'-bis(trifluoromethoxy)biphenyl as a viscous oil, which crystallized to a white solid on scratching, mp 67.5°–68° C.; $^1$H NMR ($\delta$, CDCl$_3$) 3.82 (s, 4H), 6.59 (d, 2H), 6.63 (d, 2H), 7.08 (d, 2H); $^{19}$F NMR −57.5 ($\delta$, CDCl$_3$). Anal. Calcd for C$_{14}$H$_{10}$F$_6$N$_2$O$_2$: C, 47.74; H, 2.86; N, 7 95; F, 32.36. Found: F, 33.3. Analysis of another sample prepared in the same fashion found C, 47.75; H, 2.96; N, 8.01; F, 28.73.

EXAMPLE 2

Synthesis of 3-(Perfluoro-2-chloro-3-oxahexyloxy)nitrobenzene

To a mixture of 19.3 g (0.072 mol) of perfluoropropyl perfluorovinyl ether and 16.3 g (0.069 mol) of hexachloroethane in 25 mL of dimethylformamide (DMF) at about 0° C. under argon was added 6.85 g (0.043 mol) of solid sodium 3-nitrophenoxide over 14 min. The solid was rinsed into the flask with an additional 15 mL of DMF. The mixture was allowed to warm to room temperature and stirred for about 3 days. It was then poured into ice water containing 5 mL of concentrated hydrochloric acid and extracted with 2×100 mL of ether. The combined ether extracts were washed with 2×50 mL of water and dried over anhydrous magnesium sulfate. The solution was concentrated on a rotary evaporator and then distilled in a Kugelrohr apparatus. After removing lower boiling materials, the product was distilled at a bath temperature of 85°–95° C. and 0.5 mm pressure to give 16.6 g (89%) of 3-(perfluoro-2-chloro-3-oxahexyloxy)nitrobenzene as a clear oil; $^1$H NMR ($\delta$, CDCl$_3$) 7.63 (m, 2H), 8.10 (s, 1H), 8.23 (m, 1H); $^{19}$F NMR ($\delta$, CDCl$_3$) −79.8 (1F), −81.6 (3F), −85.2 (AB quartet with fine structure, 2F); −87.3 (2F), −130.4 (2F). Anal. Calcd for C$_{11}$H$_4$ClF$_{10}$NO$_4$: C, 30.05; H, 0.92; N, 3.12; Cl, 8.06; F, 43.22. Found: C, 29.79; H, 0.82; N, 3.54; Cl, 8.39; F, 40.19.

EXAMPLE 3

Synthesis of 4,4'-Diamino-2,2'-bis(perfluoro-2-chloro-3-oxahexyloxy)biphenyl

The nitro-compound from Example 2 (124.3 g, 0.282 mol) was reacted with sodium borohydride (64.01 g, 1.69 mol) in DMSO as described in Example 1 to give 102.9 g of the intermediate hydrazo-compound. A 58.3 g portion of this product in 200 mL of ether was added over 1 h to a mixture of 88 g tin(II) chloride, 250 mL of concentrated hydrochloric acid, 150 mL of ether, and 200 mL of methylene chloride at 0° C. The resulting mixture was stirred for 96 h at room temperature. The mixture was warmed in a water bath to remove the organic solvents, and the aqueous solution was decanted, leaving a gum. The gum was treated with 200 mL of 10% aqueous sodium hydroxide and 300 mL of ether. The mixture was filtered through Celite ®. The ether layer was separated, dried over anhydrous magnesium sulfate, and concentrated on a rotary evaporator. The residue was dissolved in methylene chloride, dried again over anhydrous magnesium sulfate, and concentrated on a rotary evaporator to an oil. Kugelrohr distillation at 127°–160° C. and 0.3 mm pressure gave 48.0 g of oil. Spectroscopic and thin layer chromatographic analysis of the oil suggested a mixture of products and, after several unsuccessful attempts to separate the products by crystallizations as the amine hydrochloride salts, the material was chromatographed on a 14" (35.6 cm) long by 2" (5.1 cm) diameter column of silica gel. The column was eluted with mixtures of hexane and ethyl acetate from 10:1 to 3:1, taking 50 mL fractions. An oil isolated from fractions 8–30 gave 11.3 g of 4,4'-diamino-2,2'-bis(perfluoro-2-chloro-3-oxahexyloxy)biphenyl on Kugelrohr distillation at 0.3 mm pressure; $^1$H NMR ($\delta$, CDCl$_3$) 3.78 (s, 4H), 6.60 (d, 2H), 6.57 (d, 2H), 7.05 (d, 2H); $^{19}$F NMR , CDCl$_3$) −80.0 (2F), −81.8 (6F), −85.3 (AB quartet with fine structure, 4F); −87.3 (2F), −130.5 (4F).

EXAMPLE 4

Synthesis of an Aramid from 4,4'-Diamino-2,2'-bis(trifluoromethoxy)biphenyl and Terephthaloyl Chloride A 300 mL four-necked flask equipped with a mechanical stirrer, condenser, and thermometer was charged under nitrogen with 7.04 g of anhydrous lithium chloride. The apparatus was flame-dried under argon and cooled to room temperature. The flask was charged with 2.7252 g (7.715 mmol) of the title diamine, 48 mL of N-methylpyrollidone (NMP) (freshly distilled from calcium hydride), and 48 mL of tetramethylurea (TMU)

(freshly distilled from calcium hydride). The mixture was warmed to 40°–45° C. for 0.5 h and then cooled to −5° C. in an ice/salt bath. Terephthaloyl chloride (1.5676 g, 7.7212 mmol) was added in one portion, followed by an additional 48 mL of TMU. The mixture was stirred for 1 h at about 0° C. and then warmed to 72° C. and maintained for 20 h. The viscous solution was cooled to 40° C. and slowly poured with vigorous stirring into 3 L of ice water. The solid was collected, washed with 2×1 L water and 2×80–120 mL of ice water, rinsed twice with acetone and ether, and dried at 90° C. and 0.05 mm pressure to give 3.51 g of off-white solid polymer having an inherent viscosity of 5.36 dL/g in dimethylacetamide (DMAC) containing 5% lithium chloride. A clear and nearly colorless film could be cast from a DMAC solution. By TGA, the polymer showed a 10% weight loss temperature of about 490° C. when heated under nitrogen at 25°/min.

EXAMPLE 5

Synthesis of a Polyimide from 4,4'-Diamino-2,2'-bis(trifluoromethoxy)biphenyl and Pyromellitic Dianhydride A flame-dried 50-mL flask equipped with a mechanical stirrer, condenser, and thermometer was charged under argon with 2.7851 g (7.907 mmol) of 4,4'-diamino-2,2'-bis(trifluoromethoxy)biphenyl and 22.5 mL of NMP (freshly distilled form calcium hydride). The flask was cooled in an ice/acetone bath and 1.7246 g (7.907 mmol) of pyromellitic dianhydride was added. The mixture was stirred for 3 h in the cooling bath. A small aliquot of the solution was removed and the intermediate polyamic acid was precipitated in water and dried. This material showed an inherent viscosity of 0.48 dL/g in dimethylacetamide. A second aliquot of the solution was cast as a 0.4 μm film on a glass plate and dried at 80° C. to give a strong colorless film. The film was cured by heating: 130° C. for 1 min, 130°–200° C. at 10°/min, 200° C. for 1 min, 200°–270° C. at 10°/min, and 270° C. for 10 min.

EXAMPLE 6

Synthesis of a Polyimide from 4,4'-Diamino-2,2'-bis(trifluoromethoxy)biphenyl and Biphenyl Dianhydride The procedure of Example 5 was followed using 2.3274 g of biphenyl dianhydride in place of the pyromellitic dianhydride, giving an intermediate polyamic acid with an inherent viscosity of 0.575 dL/g and a polyimide film by subjecting a cast film of the polyamic acid to the same curing temperature profile.

EXAMPLE 7

Synthesis of a Poly(amic Acid) Based on 3,3',4,4'-Biphenyltetracarboxylic Dianhydride and 2,2'-Bis(trifluoromethoxy)benzidine and Preparation of Polyimide Film therefrom A 100 mL reaction kettle, fitted with a nitrogen inlet and outlet and a mechanical stirrer, was charged with 3.6410 g (12.375 mmol) of 3,3',4,4'-biphenyltetracarboxylic dianhydride and 4.3569 g (12.375 mmol) of 2,2'-bis(trifluoromethoxy)benzidine. Shortly thereafter, 32 mL of N-methyl-2-pyrrolidone (NMP) was added and stirring begun. The heterogeneous, yellow solution was allowed to stir at room temperature overnight (ca. 18 h). The next day, the homogeneous, viscous, yellow solution was diluted to 16 wt % solids (from 20 wt % solids) with NMP. The solution was allowed to stir at room temperature overnight (ca. 18 h) to equlibrate. The following day, the still homogeneous, viscous, yellow solution was further diluted to 14 wt % solids with NMP and was allowed to stir at room temperature for several days (ca. 56 h). Analysis of the poly(amic acid) solution by GPC revealed an $M_n$ of 165000 and an $M_w$ of 342000 ($M_w/M_n$=2.1) versus polystyrene standards (DMAC/LiBr/H$_3$PO$_4$/THF solvent system). The solution was then pressured filtered through a 5 μm polypropylene filter for spincoating onto 5" (12.7 cm) silicon wafers. After being spincoated, the wafers were immediately placed in an air oven at 135° C. for 30 min, then placed in a nitrogen-purged oven and heated to 200° C. for 30 min and then heated to 350° C. for 1 h. The resulting polyimide film was coherent and adhered well to the wafer. Etching of the oxide layer of the silicon wafer in aqueous hydrofluoric acid yielded the free-standing polyimide film, which was light-yellow but slightly hazy. The 21.4 μm film gave the following properties when tested on an Instron Model 4501 per ASTM D 882-83 (Method A): tensile strength=316 MPa, tensile elongation at break=39%, and Young's modulus=4.4 GPa.

EXAMPLE 8

Synthesis of a Poly(amic Acid) Based on Pyromellitic Dianhydride and 2,2'-Bis(trifluoromethoxy)benzidine and Preparation of Polyimide Film therefrom A 100 mL reaction kettle, fitted with a nitrogen inlet and outlet and a mechanical stirrer, was charged with 4.9405 g (14.026 mmol) of 2,2'-bis(trifluoromethoxy)-benzidine. After the benzidine was dissolved in 32 mL of N-methyl-2-pyrrolidone (NMP), 3.0594 g (14.026 mmol) of pyromellitic dianhydride was added with stirring. The solution was allowed to stir overnight at room temperature. Analysis of the poly(amic acid) solution by GPC revealed an $M_n$ of 117000 and an $M_w$ of 195000 ($M_w/M_n$=1.7) versus polystyrene standards (DMAC/LiBr/H$_3$PO$_4$/THF solvent system). The next day the resulting homogeneous, viscous, yellow solution was diluted to 13 wt % solids with successive additions of 10 and 11.5 mL of NMP. The solution was then pressure filtered through a 1 μm polypropylene filter for spincoating onto 5" (12.7 cm) silicon wafers. After being spincoated, the wafers were immediately placed in an air oven at 135° C. for 30 min, then placed in a nitrogen-purged oven and heated to 200° C. for 30 min and then heated to 350° C. for 1 h. The resulting polyimide film was coherent and adhered well to the wafer. Etching of the oxide layer of the silicon wafer in aqueous hydrofluoric acid yielded the free-standing polyimide film, which was light-yellow and transparent. The 12.0 μm film gave the following properties when tested on an Instron Model 4501 per ASTM D 882-83 (Method A): tensile strength=378 MPa, tensile elongation at break=18%, and Young's modulus=7.2 GPa.

EXAMPLE 9

Synthesis of a Poly(amic acid) Based on 9,9'-Bis(trifluoromethyl)xanthene-2,3,6,7-dianhydride and 2,2'-Bis(trifluoromethoxy)benzidine and Preparation of Polyimide Film therefrom A 100 mL reaction kettle fitted with a mechanical stirrer and nitrogen inlet and outlet was charged with 4.5231 g (9.8708 mmol) of 9,9'-bis(trifluoromethyl)xanthene-2,3,6,7-dianhydride and 3.4769 g (9.8708 mmol)

of 2,2'-bis(trifluoromethoxy)benzidine. Shortly thereafter, 32 mL of N-methyl-2-pyrrolidone (NMP) was added and stirring begun. The initially heterogeneous, pale yellow solution was stirred at room temperature overnight (ca. 18 h). The next day the homogeneous, viscous, pale yellow solution that resulted was diluted to 16 wt % (from the original 20 wt %) with NMP. The solution was equilibrated by stirring overnight (ca. 18 h). Analysis of the poly(amic acid) solution by GPC revealed an $M_n$ of 107000 and an $M_w$ of 217000 ($M_w/M_n=2.02$) versus polystyrene standards (DMAC/LiBr/H$_3$PO$_4$/THF solvent system). The following day the solution was pressure filtered through a 1 μm polypropylene filter for spincoating onto 5" (12.7 cm) silicon wafers. After being spincoated, the wafers were immediately placed in an air oven at 135° C. for 30 min, then placed in a nitrogen-purged oven and heated to 200° C. for 30 min and then heated to 350° C. for 1 h. The resulting polyimide film was coherent and adhered well to the wafer. Etching of the oxide layer of the silicon wafer in aqueous hydrofluoric acid yielded the free-standing polyimide film, which was almost colorless. The 10.1 μm film gave the following properties when tested on an Instron Model 4501 per ASTM D 882-83 (Method A): tensile strength=411 MPa, tensile elongation at break=18%, and Young's modulus=5.1 GPa. The coefficient of thermal expansion (CTE) of the film measured by TMA (10°/min, 0°-200° C.) was 10 ppm. The dielectric constant of a dried film was 2.8, and the TGA (15°/min, room temp. to 600° C.) revealed the onset of weight loss to be about 444° C. under the chosen conditions.

EXAMPLE 10

Synthesis of a Poly(amic acid) Based on 9-Phenyl-9'-trifluoromethylxanthene-2,3,6,7-dianhydride and 2,2'-bis(trifluoromethoxy)benzidine and Preparation of Polyimide Film therefrom A 100 mL reaction kettle fitted with a mechanical stirrer and anitrogen inlet and outlet was charged with 4.5574 g (9.773 mmol) of 9-phenyl-9'-trifluoromethylxanthene-2,3,6,7-dianhydride and 3.4426 g (9.773 mmol) of 2,2'-bis(trifluoromethoxy)benzidine. Shortly thereafter, 32 mL of N-methyl-2-pyrrolidone (NMP) was added and stirring begun. After complete dissolution, the homogeneous, pale yellow solution was stirred at room temperature overnight (ca. 18 h). The next day, the homogeneous, very pale yellow, viscous solution was diluted to 14 wt % solids (from the original 20 wt % solids) with NMP. The solution was equilibrated by stirring at room temperature overnight (ca. 18 h). Analysis of the poly(amic acid) solution by GPC revealed an $M_n$ of 149000 and an $M_w$ of 354000 ($M_w/M_n=2.36$) versus polystyrene standards (DMAC/LiBr/H$_3$PO$_4$/THF solvent system). The following day, the solution was pressure filtered through a 5 μm polypropylene filter for spincoating onto 5" (12.7 cm) silicon wafers. After being spincoated, the wafers were immediately placed in an air oven at 135° C. for 30 min, then placed in a nitrogen-purged oven and heated to 200° C. for 30 min and then heated to 350° C. for 1 h. The resulting polyimide film was coherent and adhered well to the wafer. Etching of the oxide layer of the silicon wafer in aqueous hydrofluoric acid yielded the free-standing polyimide film, which was pale-yellow. The 23.4 μm film gave the following properties when tested on an Instron Model 4501 per ASTM D 882-83 (Method A): tensile strength=143 MPa, tensile elongation at break=7%, Young's modulus=3.4 GPa, onset of weight loss at about 421° C., CTE=36 (5°/min, 0°-200° C.).

EXAMPLE 11

Synthesis of Polyimide Based on 9-Phenyl-9'-trifluoromethylxanthene-2,3,6,7-dianhydride and 2,2'-Bis(trifluoromethoxy)benzidine A 100 mL reaction kettle, fitted with a nitrogen inlet and outlet and a mechanical stirrer, was charged with 3.4181 g (7.330 mmol) of 9-phenyl-9'-trifluoromethylxanthene-2,3,6,7-dianhydride and 2.5819 g (7.330 mmol) of 2,2'-bis(trifluoromethoxy)benzidine. Shortly thereafter, 24 mL of an N-methyl-2-pyrrolidone/N-cyclohexyl-2-pyrrolidone (NMP/CHP of 4/1, v/v) solvent mixture was added, and stirring was begun. The solution was initially heterogeneous, but homogenized slowly as the monomers dissolved. The viscosity increased noticeably within ca. 10 min of stirring at room temperature. Stirring at room temperature was continued overnight (ca. 18 h). Analysis of the poly(amic acid) solution by GPC revealed an $M_n$ of 100000 and an $M_w$ of 223000 ($M_w/M_n=2.21$) versus polystyrene standards (DMAC/LiBr/H$_3$PO$_4$/THF solvent system). The next day the extremely viscous, very pale-yellow solution was diluted to ca. 10 wt % solids (from the original 20 wt % solids) with the NMP/CHP (4/1) solvent mixture. The reaction kettle was the fitted with a Dean-Stark trap and water condenser on the outlet side for thermal imidization. The reaction kettle was heated in a temperature controlled oil bath to 180°-190° C. and stirred overnight (ca. 18 h). The following day the pale-yellow homogeneous solution was cooled to room temperature, which resulted in the solution becoming a white wax-like gel. The solution was again heated, via the oil bath, to redissolve the solid and diluted to 6 wt % solids with NMP. Cooling to room temperature again caused formation of the gel-like solid. The heterogeneous solution was poured into ca. 1 L of methanol to precipitate the polyimide as a solid. The solid was collected by filtration followed by air drying for ca. 1 h and then drying in a vacuum oven at ca. 60° C. overnight (ca. 18 h). The solid was also found to be soluble in hot DMAC.

EXAMPLE 12

Synthesis of 4,4'-Diamino-2,2'-bis(perfluoro-2-hydro-3-oxahexyloxy)biphenyl 3-(Perfluoro-2-hydro-3-oxahexyloxy)nitrobenzene (225.7 g, 0.557 mol), prepared by reaction of 3-nitrophenol with perfluoropropyl perfluorovinyl ether, was reacted with sodium borohydride (66.20 g, 1.75 mol) in DMSO as described in Example 1 to give 191.1 g of the intermediate hydrazo compound. A 65.1 g portion of this product in 75 mL of methylene chloride and 50 mL of ether was added dropwise to a solution of 400 mL of concentrated hydrochloric acid and 40 g of stannous chloride at −40° C. An additional 50 mL of methylene chloride was added and the solution was stirred and allowed to warm to room temperature; stirring was continued overnight. The mixture was concentrated on a rotary evaporator at 350° C. to remove the organic solvents, and the aqueous solution was decanted from a gum. The gum was rinsed with water and stirred with 1 L of ether and 500 mL of 10% aqueous potassium hydroxide solution. The aqueous phase was saturated with sodium chloride and separated from the ether solution. The ether solution was dried over anhydrous magnesium sulfate and concentrated on a rotary evaporator to 63.15 g of dark oil. A Kugelrohr distillation of the oil at 149°–163° C. and 0.3 mm pressure gave 53.85 g of oil, which was determined to be a mixture of isomers by NMR spectroscopy. The product was chromatographed on a 6×34 cm column of silica gel, eluting with 5% ethyl acetate in hexane (5.7 L), followed by 10% ethyl acetate in hexane (2.6 L). The desired product (15.9 g) was isolated from the 10% ethyl acetate in hexane fractions and Kugelrohr distilled at 150°–160° C. and 0.3 mm pressure; $^1$H NMR ($\delta$, CDCl$_3$) 3.78 (s, 4H), 5.70 (dt, 2H), 6.57 (d, 2H), 6.65 (s, 2H), 7.03 (d, 2H).

EXAMPLE 13

Synthesis of 4,4′-Diamino-2,2′-bis(1,1,2,2-tetrafluoroethoxy)biphenyl

1-Nitro-3-(1,1,2,2-tetrafluoroethoxy)benzene (75 g, 0.31 mol) (purchased from the Aldrich Chemical Company, Milwaukee, Wis.) was reacted with sodium borohydride (43.1 g, 1.14 mol) in DMSO as described in Example 1 to give 60.1 g of the intermediate hydrazo compound. A 78.26 g portion of this product (from two preparations) in 150 mL of ether was added dropwise to an ice-water cooled mixture of 500 mL of concentrated hydrochloric acid, 15 g of stannous chloride, 300 mL of ether, and 200 mL of methylene chloride. The mixture was stirred and allowed to warm to room temperature; stirring was continued overnight. The mixture was diluted with an additonal 200 mL of concentrated hydrochloric acid and the organic solvents removed by distillation. A white solid was removed by filtration and stirred with 300 mL of ether and 300 mL of 10% aqueous sodium hydroxide solution. The ether solution was dried over anhydrous magnesium sulfate and concentrated on a rotary evaporator to 16.71 g of dark oil. A Kugelrohr distillation of the oil at 135°–180° C. and 0.2 mm pressure gave 12.65 g of oil. The initial filtrate was made basic (pH 11) by adding 50% aqueous sodium hydroxide solution and extracted with ether. This ether solution, when processed as above, provided another 58 g of oil. The combined products were determined by NMR spectroscopy to be a mixture of the desired product and another isomer in a ratio of about 2:1. The product was purified by dissolving it in about 500 mL of methylene chloride, which was then saturated with gaseous hydrogen chloride. The precipitated product was collected and converted to the free diamine by stirring with ether and 10% aqueous sodium hydroxide solution. The ether solution was dried over anhydrous magnesium sulfate and concentrated on a rotary evaporator. The purification process was repeated twice to give 22.97 g of the desired product after a Kugelrohr distillation at 150° C. and 0.2 mm; $^1$H NMR ($\delta$, CDCl$_3$) 3.77 (s, 4H), 5.58 (tt, 2H), 6.55 (d, 2H), 6.64 (s, 2H), 7.05 (d, 2H); 1H$_{19F}$ NMR ($\delta$, CDCl$_3$) −88.63 (s, 4F), −137.32 (dt, 4F). Anal: Calcd. for C$_{16}$H$_{12}$F$_8$N$_2$O$_2$: C, 46.16; H, 2.90; N, 6.73. Found: C, 45 46; H, 3.35; N, 6.34.

Although preferred embodiments of the invention have been described hereinabove, it is to be understood that there is no intention to limit the invention to the precise constructions herein disclosed, and it is to be further understood that the right is reserved to all changes coming within the scope of the invention as defined by the appended claims.

What is claimed is:

1. A polyimide structure comprising the repeat unit:

$$\left[ \begin{array}{c} \text{structure VI} \end{array} \right]$$

wherein R$_f$ is a linear or branched perfluorinated alkyl group containing 1–18 carbon atoms or where said perfluorinated alkyl group has one F atom replaced by hydrogen or where said perfluorinated alkyl group has one F atom replaced by chlorine, or where said perfluorinated group has one F atom replaced by hydrogen and another F atom replaced by chlorine, R$_f$ optionally containing one or more ether oxygens between alkyl segments, and Y is a tetravalent hydrocarbyl group.

2. The polyimide of claim 1 wherein R$_f$ contains no H or Cl.

3. The polyimide of claim 2 wherein R$_f$ is —CF$_3$.

4. The polyimide structure of claim 1 wherein functional groups useful for crosslinking are incorporated into the chain.

5. The polyimide structure of claim 4 wherein the functional groups useful for crosslinking are selected from maleimide, nadimide, phenylacetylene (ethynylphenyl), styrene, biphenylene, benzocyclobutene, paracyclophane, and benzonitrile.

6. The polyimide of claim 1 that is a copolymer.

* * * * *